United States Patent
Tsai et al.

(10) Patent No.: US 9,855,541 B2
(45) Date of Patent: Jan. 2, 2018

(54) METHOD FOR FABRICATING THREE-DIMENSIONAL NETWORK STRUCTURE MATERIAL

(71) Applicant: Taiwan Carbon Nanotube Technology Corporation, Miaoli County (TW)

(72) Inventors: Chun-Hsien Tsai, Miaoli County (TW); Chun-Jung Tsai, Miaoli County (TW); Ting-Chuan Lee, Miaoli County (TW); Ching-Tung Hsu, Miaoli County (TW); Chia-Hung Li, Miaoli County (TW); Wan-Ju Chen, Miaoli County (TW); Jui-Yu Jao, Miaoli County (TW)

(73) Assignee: Taiwan Carbon Nano Technology Corporation, Zhunan Township, Miaoli County (TW)

( * ) Notice: Subject to any disclaimer, the term of this patent is extended or adjusted under 35 U.S.C. 154(b) by 134 days.

(21) Appl. No.: 14/517,439

(22) Filed: Oct. 17, 2014

(65) Prior Publication Data
US 2015/0148433 A1    May 28, 2015

(30) Foreign Application Priority Data
Nov. 25, 2013    (TW) .............................. 102142806 A

(51) Int. Cl.
*B01J 13/00*    (2006.01)
*A61L 26/00*    (2006.01)
(Continued)

(52) U.S. Cl.
CPC ......... *B01J 13/0065* (2013.01); *A61L 26/008* (2013.01); *A61L 26/0023* (2013.01);
(Continued)

(58) Field of Classification Search
CPC ................ A61L 26/0023; A61L 26/008; B01J 13/0091; B01J 20/28047; C08L 1/286
See application file for complete search history.

(56) References Cited

U.S. PATENT DOCUMENTS 4,618,491 A * 10/1986 Kanematu ............ A61K 8/0212
                                                              514/781
8,591,857 B2 * 11/2013 Backov ................ B01J 13/0091
                                                              423/447.2
(Continued)

Primary Examiner — Michael A Salvitti
(74) Attorney, Agent, or Firm — Muncy, Geissler, Olds & Lowe, P.C.

(57) ABSTRACT

A method for fabricating a three-dimensional network structure material comprises steps: mixing ammonium carboxymethyl cellulose with water or with water and a nanomaterial to form a first gel or a second gel; freeze-drying the first gel or the second gel to sublimate the first gel or the second gel and form a first product or a second product; and heating the first product or the second product at a lower temperature to cure the first product or the second product and obtain a first 3D network structure material or a second 3D network structure material. The present invention uses a simple process using water as the solvent, meeting the environment protection demand and having high economical efficiency. The first and second 3D network structure materials fabricated by the present invention absorb water but do not dissolve in water. Thus, the present invention can be applied to many fields.

18 Claims, 2 Drawing Sheets

(51) Int. Cl.
  *B01J 20/28*      (2006.01)
  *C08L 1/28*       (2006.01)
(52) U.S. Cl.
  CPC ..... *B01J 13/0091* (2013.01); *B01J 20/28047* (2013.01); *C08L 1/286* (2013.01)

(56) References Cited

U.S. PATENT DOCUMENTS

2009/0123985 A1* 5/2009 Chen Yang ......... C01B 33/1585
                                                     435/176
2010/0092371 A1* 4/2010 Backov ................ B01J 13/0091
                                                     423/460
2015/0148433 A1* 5/2015 Tsai ..................... B01J 13/0065
                                                     516/106

* cited by examiner

METHOD FOR FABRICATING THREE-DIMENSIONAL NETWORK STRUCTURE MATERIAL

FIELD OF THE INVENTION

The present invention relates to a material fabrication method, particularly to a method for fabricating a three-dimensional network structure material.

BACKGROUND OF THE INVENTION

Aerogel is a solid material with a porosity of over 95%. Although aerogel is lightweight, it has superior mechanical strength. Further, aerogel features low thermal conductivity, low acoustic conduction speed and low permittivity. Aerogel can be used to produce thermal insulating materials, sound insulating materials, electrical insulating materials and absorptive materials. Therefore, aerogel is a promising material, and many researchers have been devoted to studying and improving aerogel.

A US Patent No. US 2009/0123985 disclosed a method for fabricating an aerogel and applications thereof to biocomposite materials, wherein different amounts of different ion solutions are used to modify the pore size and specific surface area of the aerogel. The aero fabricated thereby is used to produce organic/inorganic composite materials and biocomposite materials, which are to be used as materials for absorption, catalysis, separation, and medicine release. The ion solutions used by the prior art are non-volatile, inflammable, easy to prepare, easy to separate and easy to recycle. Therefore, the process of the prior art meets the global trend of environmental protection. Further, the prior art does not adopt the traditional supercritical fluid process to fabricate aerogel. Therefore, the prior art is free from the complicated procedures of the traditional supercritical fluid process and exempted from the risk of explosion of the traditional supercritical fluid process.

The safety of aerogel is dependent on the source materials thereof. If the source materials have toxics or carcinogens, the aerogel fabricated therefrom will be toxic or carcinogenic also. Polyvinyl alcohol (PVA) does not carry significant toxicity and is usually used as the source material of aerogel. The aerogel fabricated with small-molecule PVA lacks industrial applicability because it is likely to dissolve in water. Therefore, aerogel is usually fabricated with large-molecule PVA. However, large-molecule PVA is hard to dissolve in water. Thus, large-molecule PVA is usually dissolved in an organic solvent, such as toluene, in fabricating aerogel. While toluene is used as the organic solvent, the aerogel fabrication process must involve waste liquid treatment. Further, the aerogel fabrication apparatuses need chilling because the melting point of toluene is very low (−95° C.). Therefore, the traditional aerogel technology still has room to improve because of the problems of waste liquid treatment and high energy consumption.

SUMMARY OF THE INVENTION

The primary objective of the present invention is to solve the problem that the aerogels fabricated with some polymeric materials are likely to dissolve in water and lack industrial applicability, and the problem that the traditional aerogel fabrication technologies using organic solvents need extra waste liquid treatment and consume much more energy.

To achieve the abovementioned objective, the present invention proposes a method for fabricating a three-dimensional network structure material, which comprises Step 1: mixing ammonium carboxymethyl cellulose with water to form a first gel;

Step 2: freeze-drying the first gel to sublimate the first gel and remove water from the first gel to form a first product; and Step 3: undertaking a low-temperature heating process at a temperature of 50-380° C. to cure the first product and obtain a first three-dimensional network structure material.

The present invention further proposes another method for fabricating a three-dimensional network structure material, which comprises Step A: mixing a nanomaterial and ammonium carboxymethyl cellulose with water to form a second gel;

Step B: freeze-drying the second gel to sublimate the second gel and remove water from the second gel to form a second product; and Step C: undertaking a low-temperature heating process at a temperature of 50-380° C. to cure the second product and obtain a second three-dimensional network structure material.

In brief, the present invention mixes ammonium carboxymethyl cellulose with water or with water and a nanomaterial to form a first gel or a second gel, and undertakes a freeze-drying process and a low-temperature heating process of the first gel or the second gel to form a first three-dimensional network structure material or a second three-dimensional network structure material. The present invention discloses a simple aerogel fabrication process using water as the solvent, exempted from waste liquid treatment, consuming less energy, meeting environmental protection demand, and having high economical efficiency. The first three-dimensional network structure material and the second three-dimensional network structure material fabricated by the present invention absorb water but do not dissolve in water. Therefore, the products of the present invention are very useful in many fields.

DETAILED DESCRIPTION OF THE PREFERRED EMBODIMENTS

The technical contents of the present invention will be described in detail in cooperation with drawings below.

Figure 1A:
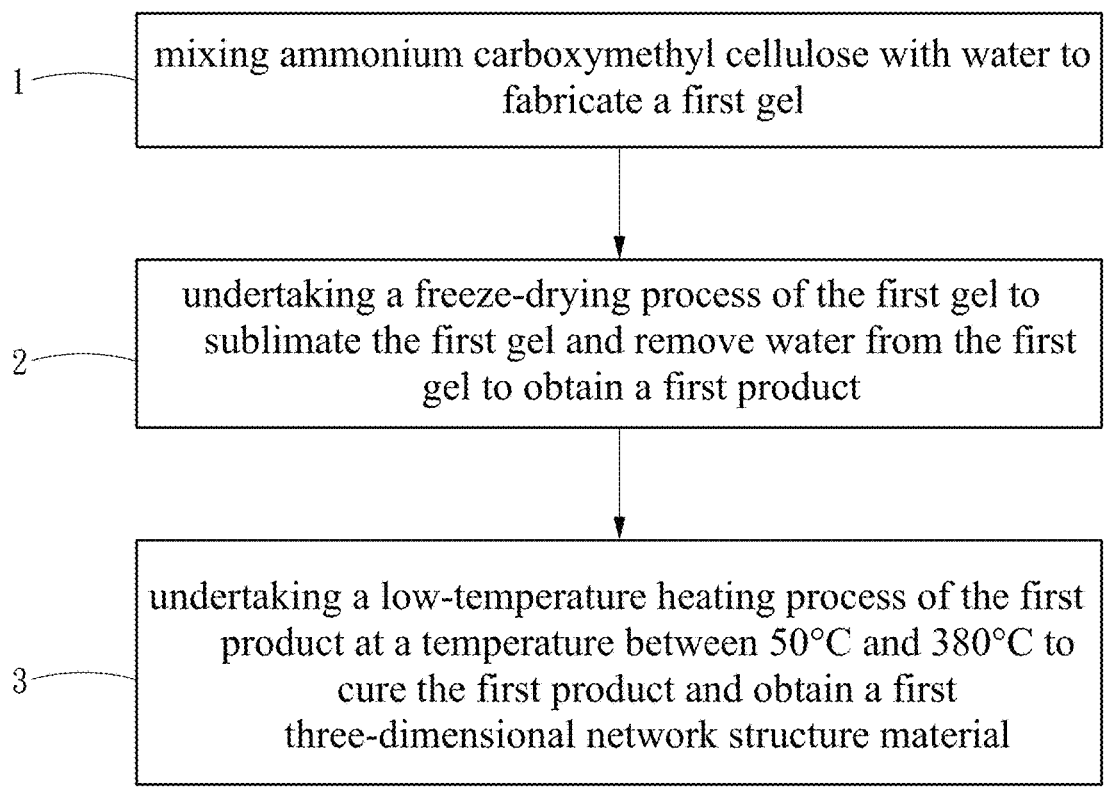
FIG. 1A is a flowchart of a method for fabricating a three-dimensional network structure material according to a first embodiment of the present invention.
Figure 1B:
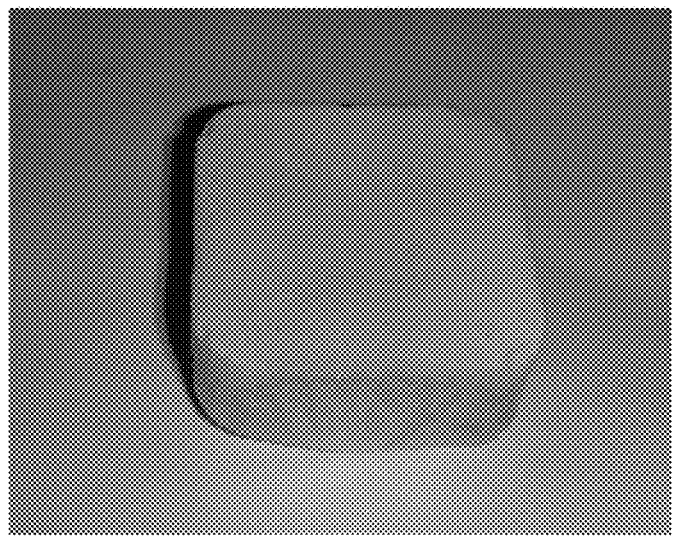
FIG. 1B shows the appearance of a three-dimensional network structure material fabricated according to the first embodiment of the present invention.

Refer to FIG. 1A and FIG. 1B. FIG. 1A is a flowchart of a method for fabricating a three-dimensional network structure material according to a first embodiment of the present invention. FIG. 1B shows the appearance of a three-dimensional network structure material fabricated according to the first embodiment of the present invention. In the first embodiment, the method for fabricating a three-dimensional network structure material of the present invention comprises Steps 1-3.

In Step 1, mix ammonium carboxymethyl cellulose with water to form a first gel. In the first embodiment, ammonium carboxymethyl cellulose and water is mixed by a weight ratio of 0.1:100-50:100 and mechanically agitated to have a gelatinous state and form a first gel. In one embodiment, a first surfactant is added to the ammonium carboxymethyl cellulose and water in fabricating the first gel. In one embodiment, the first surfactant is sodium dodecyl sulfate or sodium dodecyl sulphonate. The weight ratio of the first surfactant to water is between 0.01:100 and 50:100. While the first surfactant is used, the weight ratio of ammonium carboxymethyl cellulose to water can be modified to be between 0.1:100 and 80:100.

In Step 2, freeze-dry the first gel to sublimate the first gel and remove water from the first gel to obtain a first product. In one embodiment, a freeze-dryer chills the first gel to a temperature between 0° C. and −200° C. to sublimate the first gel and remove water from the first gel. Thereby, a first porous structure is spontaneously generated inside the first product. The weight ratio of ammonium carboxymethyl cellulose to water and the amount of the first surfactant in Step 1 is used to modify the pore size of the first porous structure.

In Step 3, undertake a low-temperature heating process at a temperature of 50-380° C. to cure the first product and obtain a first 3D reticular-structured material. In one embodiment, an oven is used to heat the first product to a temperature, preferably between 80° C. and 350° C., for a time interval between 1 minute and 10 hours to cure the first product, whereby the first product becomes insoluble in water. In the first embodiment, the first product is heated to a temperature of 140° C., which is sufficient to cure the first product into the first three-dimensional network structure material.

In one embodiment, glycerol is added to ammonium carboxymethyl cellulose and water in the fabrication of the first gel in Step 1 to enhance the mechanical properties of the first three-dimensional network structure material. The weight ratio of glycerol to ammonium carboxymethyl cellulose is between 0.01:1 and 5:1.

Figure 2A:
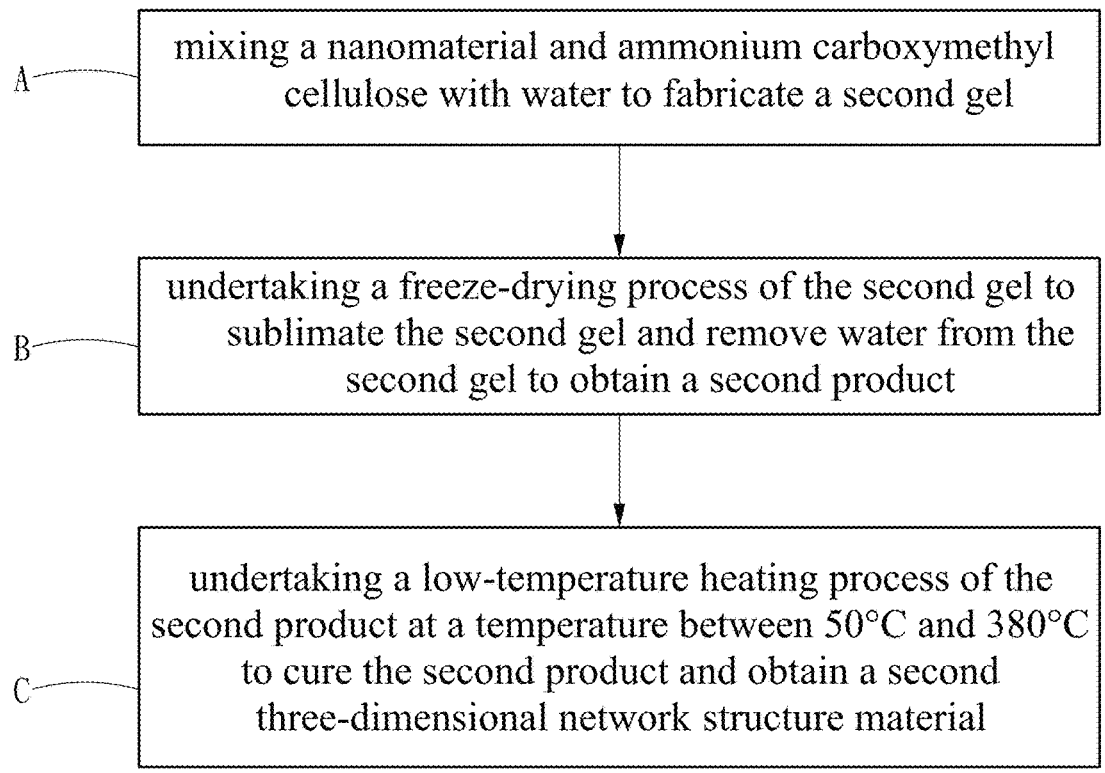
FIG. 2A is a flowchart of a method for fabricating a three-dimensional network structure material according to a second embodiment of the present invention.
Figure 2B:
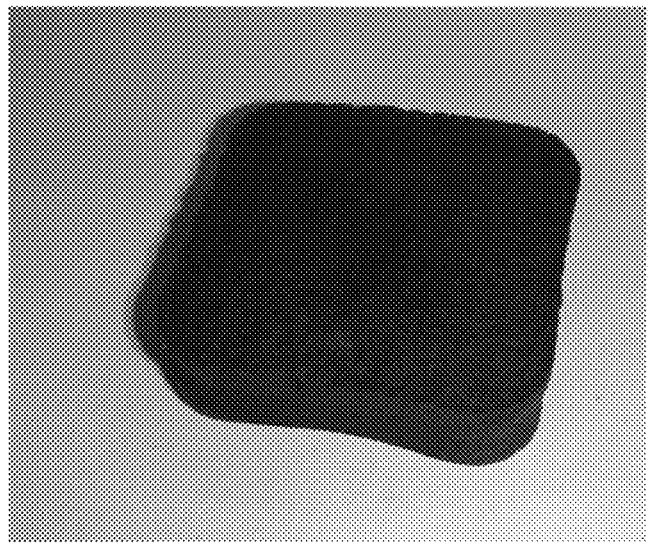
FIG. 2B shows the appearance of a three-dimensional network structure material fabricated according to the second embodiment of the present invention.

Refer to FIG. 2A and FIG. 2B. FIG. 2A is a flowchart of a method for fabricating a three-dimensional network structure material according to a second embodiment of the present invention. FIG. 2B shows the appearance of a three-dimensional network structure material fabricated according to the second embodiment of the present invention. In the second embodiment, the method for fabricating a three-dimensional network structure material of the present invention comprises Steps A-C. The second embodiment is different from the first embodiment in that Step A is different from Step 1. Step B and Step C of the second embodiment are similar to Step 2 and Step 3 of the first embodiment.

In Step A, mix a nanomaterial and ammonium carboxymethyl cellulose with water to form a second gel. In the present invention, the nanomaterial may be but is not limited to be carbon nanotubes, graphene, or carbon nanoribbons. The second gel can be fabricated with one of the three methods described below.

In the first method, mix the nanomaterial with water to form an aqueous dispersion liquid; next add ammonium carboxymethyl cellulose to the aqueous dispersion liquid; next mechanically agitate the aqueous dispersion liquid to form the second gel. In the first method, the weight ratio of the nanomaterial to water is between 0.01:100 and 50:100; the weight ratio of ammonium carboxymethyl cellulose to the aqueous dispersion liquid is between 0.1:100 and 50:100.

In the second method, acidify the nanomaterial; next mechanically agitate the acidified nanomaterial, ammonium carboxymethyl cellulose and water to form the second gel. In the second method, the weight ratio of the nanomaterial to water is between 0.01:100 and 50:100; the weight ratio of ammonium carboxymethyl cellulose to water is between 0.1:100 and 80:100.

In the third method, mechanically agitate the nanomaterial, ammonium carboxymethyl cellulose, water and a second surfactant to have a gelatinous state and form the second gel. In one embodiment, the second surfactant is sodium dodecyl sulfate or sodium dodecyl sulphonate. In the third method, the weight ratio of the second surfactant to water is between 0.01:100 and 50:100; the weight ratio of ammonium carboxymethyl cellulose to water is between 0.1:100 and 80:100; the weight ratio of the nanomaterial to water is between 0.01:100 and 50:100.

In Step B, freeze-dry the second gel to sublimate the second gel and remove water from the second gel to obtain a second product. In one embodiment, a freeze-dryer chills the second gel to a temperature between 0° C. and −200° C. to sublimate the second gel and remove water from the second gel. Thereby, a second porous structure is spontaneously generated inside the second product. The weight ratio of ammonium carboxymethyl cellulose to water and the amount of the second surfactant in Step A is used to modify the pore size of the second porous structure.

In Step C, undertake a low-temperature heating process at a temperature of 50-380° C. to cure the second product and obtain a second three-dimensional network structure material. In one embodiment, an oven is used to heat the second product to a temperature, preferably between 80° C. and 350° C., for a time interval between 1 minute and 10 hours to cure the second product, whereby the second product becomes insoluble in water. In the second embodiment, the second product is heated to a temperature of 140° C., which is sufficient to cure the second product into the second three-dimensional network structure material.

In one embodiment, glycerol is added to the nanomaterial, ammonium carboxymethyl cellulose and water in the fabrication of the second gel in Step A to enhance the mechanical properties of the second three-dimensional network structure material. The weight ratio of glycerol to ammonium carboxymethyl cellulose is between 0.01:1 and 5:1.

Each of the first three-dimensional network structure material and the second three-dimensional network structure material is fabricated to have a porous structure (the first porous structure and the second porous structure mentioned above). The pores of the porous structure are too tiny to be filled with other materials. However, nanomaterial is so small that it can be stuffed into the pores of the porous structure. Thus, nanomaterial can be filled into the pores to enhance the strength of the porous structure. Therefore, the second three-dimensional network structure material has better mechanical properties than the first three-dimensional network structure material. If the nanomaterial is carbon nanotubes, graphene, or carbon nanoribbons, the second three-dimensional network structure material would further possess superior electric conductivity, weatherability and corrosion resistance.

In conclusion, the present invention fabricates a three-dimensional network structure material with steps: mixing ammonium carboxymethyl cellulose with water to form a first gel; freeze-drying the first gel to sublimate the first gel and form a first product; and heating the first product at a lower temperature to cure the first product. Therefore, the present invention has a simple process. The present invention is characterized in using water as the solvent and thus exempted from waste liquid treatment and high energy consumption. Hence, the present invention meets the environment protection demand and has high economical efficiency. The first three-dimensional network structure material fabricated by the present invention absorbs water but does not dissolve in water. Thus, the first three-dimensional network structure material can be applied to many fields. Further, the present invention adds nanomaterial to the raw materials to fabricate the second three-dimensional network structure material having better mechanical properties, weatherability and corrosion resistance. Therefore, the present invention possesses utility, novelty and non-obviousness and meets the condition of a patent. Thus, the Inventor files the application for a patent. It will be appreciated if the patent is approved fast.

The present invention has been demonstrated in detail with the embodiments described above. However, these embodiments are only to exemplify the present invention but not to limit the scope of the present invention. Any equivalent modification or variation according to the spirit of the present invention is to be also included within the scope of the present invention.

What is claimed is:

1. A method for fabricating a three-dimensional network structure material comprising the following steps:
    Step 1: mixing ammonium carboxymethyl cellulose and water to form a first gel;
    Step 2: undertaking a freeze-drying process of the first gel to sublimate the first gel and remove water from the first gel to obtain a first product; and
    Step 3: undertaking a low-temperature heating process of the first product at a temperature not more than 380° C. to cure the first product and obtain a first three-dimensional network structure material.

2. The method for fabricating a three-dimensional network structure material according to claim 1, wherein in Step 1, a weight ratio of ammonium carboxymethyl cellulose to water is between 0.1:100 and 50:100.

3. The method for fabricating a three-dimensional network structure material according to claim 1, wherein a freeze-drying temperature of the freeze-drying process is between 0° C. and −200° C.

4. The method for fabricating a three-dimensional network structure material according to claim 1, wherein in Step 3, a heating temperature of the low-temperature heating process is between 80° C. and 350° C., and wherein a heating time of the low-temperature heating process is between 1 minute and 10 hours.

5. The method for fabricating a three-dimensional network structure material according to claim 1, wherein in Step 1, a first surfactant is added to the ammonium carboxymethyl cellulose and water in fabricating the first gel, and wherein the first surfactant is sodium dodecyl sulfate or sodium dodecyl sulphonate.

6. The method for fabricating a three-dimensional network structure material according to claim 5, wherein a weight ratio of ammonium carboxymethyl cellulose to water is between 0.1:100 and 80:100; a weight ratio of the first surfactant to water is between 0.01:100 and 50:100.

7. The method for fabricating a three-dimensional network structure material according to claim 1, wherein in Step 1, glycerol is added to ammonium carboxymethyl cellulose and water in fabricating the first gel, and wherein a weight ratio of glycerol to ammonium carboxymethyl cellulose is between 0.01:1 and 5:1.

8. A method for fabricating a three-dimensional network structure material comprising the following steps:
    Step A: mixing nanomaterial, ammonium carboxymethyl cellulose and water to form a second gel;
    Step B: undertaking a freeze-drying process of the second gel to sublimate the second gel and remove water from the second gel to obtain a second product; and
    Step C: undertaking a low-temperature heating process of the second product at a temperature not more than 380° C. to cure the second product and obtain a second three-dimensional network structure material.

9. The method for fabricating a three-dimensional network structure material according to claim 8, wherein in Step A, the nanomaterial is mixed with water to form an aqueous dispersion liquid; next, ammonium carboxymethyl cellulose is added to the aqueous dispersion liquid to fabricate the second gel.

10. The method for fabricating a three-dimensional network structure material according to claim 9, wherein in Step A, a weight ratio of the nanomaterial to water is between 0.01:100 and 50:100; a weight ratio of ammonium carboxymethyl cellulose to the aqueous dispersion liquid is between 0.1:100 and 50:100.

11. The method for fabricating a three-dimensional network structure material according to claim 8, wherein in Step A, the nanomaterial is acidified to form an acidified nanomaterial; next, the acidified nanomaterial is mixed with ammonium carboxymethyl cellulose and water to fabricate the second gel.

12. The method for fabricating a three-dimensional network structure material according to claim 11, wherein in Step A, a weight ratio of the nanomaterial to water is between 0.01:100 and 50:100; a weight ratio of ammonium carboxymethyl cellulose to water is between 0.1:100 and 80:100.

13. The method for fabricating a three-dimensional network structure material according to claim 8, wherein in Step A, a second surfactant is mixed with the nanomaterial, ammonium carboxymethyl cellulose and water and to fabricate the second gel, and wherein the second surfactant is sodium dodecyl sulfate or sodium dodecyl sulphonate.

14. The method for fabricating a three-dimensional network structure material according to claim 13, wherein in Step A, a weight ratio of the nanomaterial to water is between 0.01:100 and 50:100; a weight ratio of ammonium carboxymethyl cellulose to water is between 0.1:100 and 80:100; a weight ratio of the second surfactant to water is between 0.01:100 and 50:100.

15. The method for fabricating a three-dimensional network structure material according to claim 8, wherein a freeze-drying temperature of the freeze-drying process is between 0° C. and −200° C.

16. The method for fabricating a three-dimensional network structure material according to claim 8, wherein in Step C, a heating temperature of the low-temperature heating process is between 80° C. and 350° C., and wherein a heating time of the low-temperature heating process is between 1 minute and 10 hours.

17. The method for fabricating a three-dimensional network structure material according to claim 8, wherein in Step A, glycerol is added to the nanomaterial, ammonium carboxymethyl cellulose and water in fabricating the second gel, and wherein a weight ratio of glycerol to ammonium carboxymethyl cellulose is between 0.01:1 and 5:1.

18. The method for fabricating a three-dimensional network structure material according to claim 8, wherein the nanomaterial is selected from a group consisting of carbon nanotubes, graphene, and carbon nanoribbons.

* * * * *